United States Patent
Lange et al.

(10) Patent No.: US 10,011,860 B2
(45) Date of Patent: Jul. 3, 2018

(54) MASS-SPECTROMETRIC RESISTANCE DETERMINATION BY GROWTH MEASUREMENT

(71) Applicant: Bruker Daltonik GmbH, Bremen (DE)

(72) Inventors: Christoph Lange, Grasberg (DE); Katrin Sparbier, Bremen (DE)

(*) Notice: Subject to any disclaimer, the term of this patent is extended or adjusted under 35 U.S.C. 154(b) by 0 days.

(21) Appl. No.: 14/892,340

(22) PCT Filed: Apr. 3, 2014

(86) PCT No.: PCT/EP2014/000896
§ 371 (c)(1),
(2) Date: Nov. 19, 2015

(87) PCT Pub. No.: WO2014/187517
PCT Pub. Date: Nov. 27, 2014

(65) Prior Publication Data
US 2016/0083769 A1   Mar. 24, 2016

(30) Foreign Application Priority Data
May 23, 2013   (EP) .................................... 13002699

(51) Int. Cl.
| | | |
|---|---|---|
| C12Q 1/04 | (2006.01) | |
| G01N 33/68 | (2006.01) | |
| C12Q 1/18 | (2006.01) | |
| C12Q 1/34 | (2006.01) | |
| C12Q 1/44 | (2006.01) | |

(52) U.S. Cl.
CPC ............... *C12Q 1/04* (2013.01); *C12Q 1/18* (2013.01); *C12Q 1/34* (2013.01); *C12Q 1/44* (2013.01); *G01N 33/6851* (2013.01); *G01N 2333/922* (2013.01); *G01N 2333/936* (2013.01); *G01N 2496/00* (2013.01)

(58) Field of Classification Search
CPC ... C12Q 1/04; C12Q 1/18; C12Q 1/34; C12Q 1/44; G01N 33/6851; G01N 2496/00; G01N 2333/936; G01N 2333/922
See application file for complete search history.

(56) References Cited

U.S. PATENT DOCUMENTS

| | | | | |
|---|---|---|---|---|
| 4,695,548 A | * | 9/1987 | Cantor ............ | G01N 27/44773 264/4.3 |
| 4,888,284 A | * | 12/1989 | Konings ................ | C07K 16/40 435/183 |
| 6,287,872 B1 | | 9/2001 | Schurenberg et al. | |
| 6,750,038 B1 | * | 6/2004 | Nakane .................... | C12Q 1/18 435/32 |
| 8,293,496 B2 | | 10/2012 | Govorun et al. | |
| 2004/0185448 A1 | * | 9/2004 | Lopez-Avila ....... | H01J 49/0418 435/7.23 |
| 2009/0286225 A1 | | 11/2009 | Wheeler et al. | |
| 2011/0300552 A1 | * | 12/2011 | Demirev ................ | C12Q 1/025 435/6.15 |
| 2012/0264162 A1 | | 10/2012 | Govorun et al. | |

FOREIGN PATENT DOCUMENTS

| | | |
|---|---|---|
| DE | 19754978 A1 | 7/1999 |
| DE | 102006021493 B4 | 4/2010 |
| WO | 0184137 A1 | 11/2001 |
| WO | 0194910 A2 | 12/2001 |
| WO | 0246448 A2 | 6/2002 |
| WO | 2005031304 A2 | 4/2005 |
| WO | 2011154517 A1 | 12/2011 |
| WO | 2012016929 A1 | 2/2012 |
| WO | 2012023845 A1 | 2/2012 |

OTHER PUBLICATIONS

Hoppmann et al., Expression, purification and fluorine-18 radiolabelling . . . , Prot. Expr. Purif., 57(2), 143-152, 2007.
Garaguso et al., Matrix layer sample preparation . . . , Proteomics, 8(13), 2583-2595, May 2012.
Dytfeld et al., Proteomic Profiling of Multiple Myeloma (MM) Cells . . . , 52nd A.M. Soc. of Hematology, 116(21), 271-272, Nov. 2010.
Crespo et al., Proton Transfer Reaction Mass Spectrometry . . . , J. Microbiological Methods, 86, 8-15, Jan. 2011.
Dubska et al., Surface-enhanced laser desorption ionization . . . , Anaerobe, 17(6), 444-447, May 2011.
Sato et al., Ribosomal protein profiling . . . , Syst Appl Microbiol., 34(1), 76-80, Feb. 2011.
Sparbier et al., MALDI-TOF MS for functional detection . . . , Int. J. of Med. Microbiol., 301(1), 1 (63rd Meeting Society for Hygiene and Microbiology), Sep. 2011.
Griffin et al., Use of Matrix-Assisted Laser Desorption Ionization . . . , J. Clin. Microbiol., 50(9), 2918-2931, Jun. 2012.
Gustafsson et al., Internal calibrants allow high accuracy . . . , J. of Proteom., 75, 5093-5105, May 2012.

(Continued)

*Primary Examiner* — Renee Claytor
*Assistant Examiner* — Susan E. Fernandez
(74) *Attorney, Agent, or Firm* — Benoit & Côté Inc.

(57) ABSTRACT

The invention relates to a mass-spectrometric method to determine microbial resistances to antibiotics, in which the microbes are cultured in a medium comprising an antibiotic, and a mass spectrum of the microbes is acquired after they have been cultured. The method is characterized by the fact that any microbial growth taking place during the culture is mass-spectrometrically determined with the aid of a reference substance, which is added in a dosed amount and is co-measured in the mass spectrum, wherein a growth in microbes indicates the resistance to the antibiotic.

20 Claims, 2 Drawing Sheets

(56) References Cited

OTHER PUBLICATIONS

Sparbier et al., An automated evaluation algorithm . . . , Int. J. of Med. Microbiol., 302(1), 7, (63rd Meeting Society for Hygiene and Microbiology), Sep. 2012.
Gantt, S. L. et al., J Am Soc Mass Spectrom., vol. 10, pp. 1131-1137, Nov. 1999.

* cited by examiner

US 10,011,860 B2

MASS-SPECTROMETRIC RESISTANCE DETERMINATION BY GROWTH MEASUREMENT

TECHNICAL FIELD

The invention relates to a mass-spectrometric method to determine microbial resistances to antibiotics.

DEFINITIONS

Instead of the statutory "unified atomic mass unit" (u), this document uses the unit "dalton" (Da), which was added in the last (eighth) edition 2006 of the document "The International System of Units (SI)" of the "Bureau International des Poids et Mesures" on an equal footing with the atomic mass unit; as is noted there, this was primarily done in order to be able to use the units kilodalton, millidalton and similar.

For reasons of simplicity, only the term "proteins" is used in this document, although in the preferred mass range of 3,000 to 15,000 daltons it would often be better to call the proteins "peptides". The transition from the lighter peptides to the heavier proteins is fluid and not unequivocally defined.

The term "microbes" is often used here as a short form for "microorganisms". The singular "microbe" also means, as is usual in general parlance, the microbial species as well as the individual microbial cell. The plural "microbes" means the microbial cells under analysis.

BACKGROUND ART

Many species of microorganisms, particularly bacteria and unicellular fungi such as yeasts, can be identified nowadays quickly and with low error rates by means of mass spectrometry. The identification is routinely done by computing similarity values between a mass spectrum of the disrupted (lysed) microbes, particularly their soluble proteins, and similar types of reference mass spectra of known microorganisms. If the similarity values exceed certain limit values, family, genus, species and even strain can be identified. This very fast and low-cost method of identifying microorganisms has proven to be extraordinarily successful, both in large scale studies and in the daily routine in many microbiological laboratories. Depending on the instrument, 48 to 384 microbial samples can be determined at the same time; identification takes only minutes from the end of culturing a colony to the identification. The method has very low error rates, much lower than the error rates of conventional microbiological identification methods, and lower even than those of DNA analyses. There are meanwhile mass spectrometers, associated evaluation programs and libraries of reference spectra on the market which are certified as IVD products for medical diagnostics in accordance with the German Medical Devices Act (MPG) and other, national or international regulations and guidelines.

As is usual in general parlance, the term "antibiotic" means a pharmacologically active substance for the treatment of microbial infectious diseases and also substances for disinfection. The successes of penicillin led to the search for and discovery of many other antibiotics. There are broad-spectrum antibiotics, which are effective against many families of microbes, and narrow-spectrum antibiotics, which are specifically effective against individual microbe species.

Ever since penicillin was used as the first pharmacologically active substance, microbial strains have increasingly developed various types of resistance to different types of antibiotics, or acquired them from other microbes, i.e. they have acquired characteristics which allow them to weaken the effect of antibiotic substances or to neutralize their effect completely. Resistances are unfortunately common meanwhile; microbes occurring in hospitals are today resistant in the main. In some cases, it is possible to predict the resistance of a microbe transmitted within the hospital to the antibiotics usually used in the hospital; this does not apply to infections which were acquired outside the hospital.

The success of a therapy for microbial infections, which are usually life-threatening in acute situations such as sepsis, or as a secondary infection during an existing primary illness (or primary infection), often depends on the first administration of an antibiotic being effective. Targeted administration requires not only that the pathogen is identified as quickly and correctly as possible, but also that its resistance to different antibiotics is determined as quickly as possible. The conventional determination of resistance consists of a culture in the presence of an antibiotic, but this unfortunately takes a very long time: 24 to 48 hours.

In addition to culturing in the presence of antibiotics, there are also genetic methods of determining resistances. There, a resistance is detected by detecting known resistance genes in the genome of the pathogen in question. An advantage of the genetic methods consists in the fact that the resistance genes can be amplified by techniques such as polymerase chain reaction (PCR), and thus the time needed for the analysis is no longer determined by the growth rate of the bacteria. The disadvantages are that they are more expensive than routine methods and are not functional tests. A resistance gene may be present, but not be expressed, which means the bacterial strain under investigation is not resistant, but the method detects it as being resistant.

The patent DE 10 2006 021 493 B4 (V. M. Govorun and J. Franzen, 2006, corresponding to GB 2 438 066 B and U.S. Pat. No. 8,293,496 B2; called "Govorun" in the following) discloses mass-spectrometric methods for the resistance determination of microbes.

In one embodiment, protein profiles of the microbes are mass-spectrometrically measured and compared after being cultured in media with and without added antibiotics, for example. Here the microbes are cultured in centrifuge tubes with and without antibiotics, for example. After culturing, the microbes are centrifuged out, rinsed, and then disrupted with acids and acetonitrile in the centrifuge tubes so that their soluble proteins are released. A small amount (around one microliter) of this liquid with disrupted microbial cells is prepared onto the sample support, dried and then coated with a small amount of matrix solution (also around one microliter). The dissolved proteins are embedded into the matrix crystals which are produced in the drying process. The samples with matrix crystals and embedded proteins are bombarded with laser light pulses in the mass spectrometer, causing ions of the protein molecules to be formed in the vaporization plasma. Measuring their time-of-flight in a time-of-flight mass spectrometer produces the mass spectrum of the microbe, which essentially consists of the protein peaks.

The similarity between the two mass spectra allows only limited conclusions to be drawn about the resistance of the microbes. If susceptible microbes are only inhibited in their growth or killed, without being destroyed, as for example *klebsiellae* from the family of the enterobacteriaceae, the resulting mass spectrum is practically identical to that of the microbes from media without antibiotics. This is because the formation of the mass spectra which are obtained using ionization by matrix-assisted laser desorption (MALDI) is only slightly dependent on the quantity of microbes in the sample. Sample preparations with ten thousand microbes provide practically the same mass spectra as sample preparations with ten million microbes, which is ideal for an identification, but not for identifying the resistance. If merely the growth of the microbes is stopped, the same mass spectra result, because the only difference is in quantity, which does not show up in the mass spectra.

As is explained further in the Govorun patent, the resistance can also be identified by adding a second type of microbe to the microbes under investigation; this second type provides a very different mass spectrum, is resistant, and definitely continues to grow in the presence of the antibiotic. The mass spectrum with the superimposed proteins of both microbes should then show the differences in growth. Unfortunately, this method has proved to be not very practicable in routine work for various reasons: it assumes at least rough quantitative determinations of the microbes used, approximately equal growth rates in the culture medium used, and that the reference microbes are resistant to many antibiotics.

The microbes whose resistance is to be determined are preferably present in sufficient quantities in a sufficiently pure form. They can form colonies on an agar, or also exist as microbes from a blood culture, for example. With agar cultures, it is common practice to use microbes from not just one colony for the test, but to subject the microbes from at least five colonies together to this test in order to identify the possible presence of a resistant microbe among non-resistant microbes of the same species. A trained and experienced laboratory technician is generally able to recognize colonies of the same species of microbe and to harvest them. They must then be mixed and divided up for the cultures. Blood cultures naturally contain a mixture of the different microbes which were transmitted in the infection.

As a rule, a resistance determination (including one according to Govorun) is often preceded by the identification of the microbes which have grown on the agar culture or in the blood culture. It is helpful here, especially for the method according to Govorun, to know the microbe species and its growth rate. It is also usually the case that the antibiotics against which this microbe can be resistant are also known. Furthermore, the minimum inhibitory concentrations (MIC) for susceptible microbes are also usually known. This means that cultures with these antibiotics in suitable concentrations can be prepared; the minimum culture times for the Govorun method are given by the known growth rates.

In view of the foregoing, there is a need to provide a mass-spectrometric method with which the resistance of microbes to one or more antibiotics can be determined with certainty, at low cost, in a largely automated manner, and, most importantly, at high speed, in particular for fast-growing and thus especially dangerous pathogens in about an hour. It is preferable that the method can be carried out using the same routine mass spectrometers which are also used for the mass-spectrometric identification of the microbes.

DISCLOSURE OF INVENTION

The invention provides a method for the mass-spectrometric determination of microbial resistances, in which the microbes are cultured in a medium comprising an antibiotic, and a mass spectrum $MS_{cum}$ of the microbes is acquired after they have been cultured. The method according to the invention is characterized by the fact that any microbial growth taking place during the culture is determined with the aid of a reference substance, which is added in dosed amount and also measured (co-measured) in the mass spectrum $MS_{cum}$ wherein microbial growth indicates resistance to the antibiotic. Microbial growth can be ascertained by determining the quantity of microbes after culturing using mass spectrometry and then comparing this quantity with a correspondingly determined quantity of microbes before culturing and/or with a correspondingly determined quantity of microbes after culturing without the antibiotic.

A first preferred embodiment comprises determining the quantity of microbes after the culturing from the mass spectrum $MS_{cum}$ and reporting the microbes as being resistant if the quantity of microbes exceeds a specified limit value. It is advantageous here for the quantity of microbes to be standardized at the start of the culture.

A second preferred embodiment comprises additionally culturing the microbes in the medium without the antibiotic and acquiring a mass spectrum $MS_{sine}$ of the microbes after their culturing without the antibiotic. The reference substance, of which a dosed amount was added, is also measured in the mass spectrum, and the microbes are reported as resistant if the quantities of microbes derived from the mass spectra $MS_{cum}$ and $MS_{sine}$ differ in relative or absolute terms by less than a specified limit value.

A third preferred embodiment comprises additionally acquiring a mass spectrum $MS_0$ before culturing. The reference substance, of which a dosed amount was added, is also measured in the mass spectrum, and the microbes are reported as being resistant if the quantity of microbes determined from the mass spectrum $MS_{cum}$ significantly exceeds the quantity of microbes determined from the mass spectrum $MS_0$. In this embodiment the microbes can be added to the medium, which is afterwards divided into two (preferably equal-sized) cultures, which are used for culturing with the antibiotic and for the acquisition of the mass spectrum $MS_0$ respectively. On the other hand, a portion of the medium can also be removed after the antibiotic has been added, or at the same time, and used for acquiring the mass spectrum $MS_0$.

The decision criteria used in the three preferred embodiments can, if applicable, also be combined by logical operators, such as an AND operation or a non-exclusive OR operation.

The term "mass spectrum" comprises the mass-spectrometric raw data right through to a processed peak list which comprises only the positions and intensities of mass signals. A mass spectrum here can consist of a large number of intensity values in a continuous mass range, but also the intensity values of several separate mass ranges. The mass spectrum can be subjected to signal processing before the quantity of microbes is determined. This processing can, for example, comprise correction (subtraction) of the base line, smoothing of mass signals, elimination of noise signals and/or selection of mass signals above a specified noise value.

The quantity of microbes, or a measure of it, can be determined from a mass spectrum in different ways, for example by the quotient of the intensity of a microbe signal and the intensity of a reference signal or the summed intensities of several reference signals; by the quotient of the summed intensities of several microbe signals and the intensity of a reference signal or the summed intensities of several reference signals; or by the quotient of the summed intensities of all signals of a part or the whole mass spectrum and the intensity of a reference signal or the summed intensities of several reference signals. Before the summation, microbe signals can be selected from a peak list or a continuous mass spectrum, for example those which occur frequently in repeat measurements or those with a high signal intensity. In addition to peak lists, it is also possible to use mass-spectrometric raw data (even without a calibrated mass axis if the positions of the reference substances are known) to determine the quantity of microbes, for example by summing all intensity values in a selected range of the raw data and dividing by the summed intensity values in a range with a reference signal, with the base line being corrected in advance, where necessary.

The microbes can be cultured in a medium to which a single antibiotic or a mixture of different antibiotics has been added. In order to determine, or at least estimate, the strength of the resistance, the microbes can be cultured in parallel in several (two or more) cultures, each with a different concentration of an antibiotic, where a mass spectrum $MS_{cum,i}$ of the microbes and the dosed reference substances is acquired for each culture. To test resistance to several antibiotics, it is possible to simultaneously (in parallel) prepare several (two or more) cultures with several antibiotics, where necessary even with different concentration levels of the antibiotics in each case. Here again, a mass spectrum $MS_{cum,i}$ of the microbes and the dosed reference substances is acquired for each culture.

The reference substance can be added in a dosed amount to the medium before, during or after culturing, during the preparation of a mass-spectrometric sample or during the acquisition of the mass spectrum. The dosed reference substance can be added after the cell lysis of the microbes. If the reference substance is added to the medium, it must not be taken up or broken down by the microbes; if it is added after the cell lysis, this condition does essentially not apply. If the mass spectra are acquired using ionization by matrix-assisted laser desorption (MALDI), the reference substance is preferably added only when the MALDI samples are being prepared on a sample support, in particular together with the matrix solution.

It is also possible to add a mixture of reference substances in dosed amounts. It is advantageous here if a larger range of concentrations is covered by the reference substances in the mixture; three reference substances can be used in ratios of 100:10:1 or 25:5:1, for example. A reference substance should be able to be ionized efficiently and provide several identifiable reference signals in the corresponding mass spectra, if possible. It is preferable if the proton affinity of the reference substance is greater than the proton affinity of most of the microbe proteins. Preferred reference substances are ribonucleases or lysozymes. The mass of the reference substances is preferably between 10 and 20 kilodaltons, in particular between 14 and 15 kilodaltons.

The microbes under analysis are preferably present in a sufficiently pure form. They can form colonies on an agar, for example, or can be obtained from a blood culture. It is also possible to examine microbes of a sample under investigation, e.g. a swab of the nasal mucosa, directly or after a pre-multiplication in a liquid medium, using the method according to the invention. In order to carry out the method according to the invention, it is not in principle necessary that the quantity of microbes is visible to the naked eye before or after the culture, i.e. before culturing, possibly less than $10^5$ microbial cells, in particular less than $10^4$ microbial cells, are sufficient, the cultures preferably being carried out in volumes between 1 µl and 1 ml, in particular in 100 µl. A low number of microbial cells in a sample under investigation at the beginning and a short culture time can make it necessary to concentrate the proteins of the microbes before or during the preparation of a mass-spectrometric sample. The concentration can be done, for example, by precipitating the proteins after lysing the microbial cells with subsequent separation of the proteins, e.g. by centrifuging, or with the aid of surfaces functionalized for protein binding, as can be present on (magnetic) beads, on MALDI sample supports, or on the surface of the packing material of pipette tips, for example. Beads separated and loaded with proteins can be applied directly onto a MALDI sample support, where necessary.

The method according to the invention can be used to determine the resistance of bacteria, and also to determine the resistance of unicellular fungi, such as yeasts, to an antimycotic or a mixture of antimycotics. A further embodiment of the method according to the invention comprises taxonomically identifying the microbes before determining the resistance and selecting the reference substance, limit values for the determination of the resistance, the medium and/or the culture conditions, in particular the culture period, on the basis of the taxonomic classification.

One embodiment of the invention is similar to the method according to Govorun, but is directed to be able to measure the microbial growth by increases in proteins, in particular. In order to quantitatively determine the microbial growth in the media with antibiotics with the aid of their mass spectra, one or more suitable, precisely dosed reference substances are added to the culture or to the lysed cells. The increase in the biomass, and thus the proteins in particular, in media with antibiotics is determined with the aid of the reference substances. A comparison can be made here with the microbial growths in media without antibiotics, as well as a comparison with the quantity of microbes without further culturing. An increase in the biomass to an expected extent shows that the microbes investigated are resistant to the antibiotics at the concentration used; susceptible microbes show no measurable growth if the concentration of the antibiotic is above the minimum inhibitory concentration (MIC).

The method has proved to be very rapid. Since only two generations of doubling are necessary in order to make the biomass grow by a factor of four, the resistance of dangerous infections, which are usually attributable to fast-growing microbes with 20 minutes doubling time, can already be detected after a culture period of 40 minutes; slower-growing microbes require longer times. The requisite culture period can be specified when the microbe species and thus its doubling time, is known.

The invention also provides a sample support for ionization by matrix-assisted laser desorption (MALDI) with a large number of sample areas, on each of which is a thin layer of a MALDI matrix substance. The sample support is characterized by the fact that the thin layer comprises a dosed reference substance with a mass of between 10 and 20 kilodaltons, in particular between 14 and 15 kilodaltons. The thin layer can furthermore have at least two different reference substances, which differ in concentration by a factor of between 5 and 100, if required also by a factor of 1000. Furthermore, the invention provides consumable material for ionization by matrix-assisted laser desorption (MALDI). This consumable material is a freeze-dried mixture of a MALDI matrix substance and at least one reference substance. The mass of the one or more reference substances is preferably between 10 and 20 kilodaltons, in particular between 14 and 15 kilodaltons. It is preferable if the reference substances are present in different concentrations, for example in the ratio 5:1, 10:1, 100:1 or 1000:1.

PREFERRED MODE(S) FOR CARRYING OUT THE INVENTION

Figure 1:
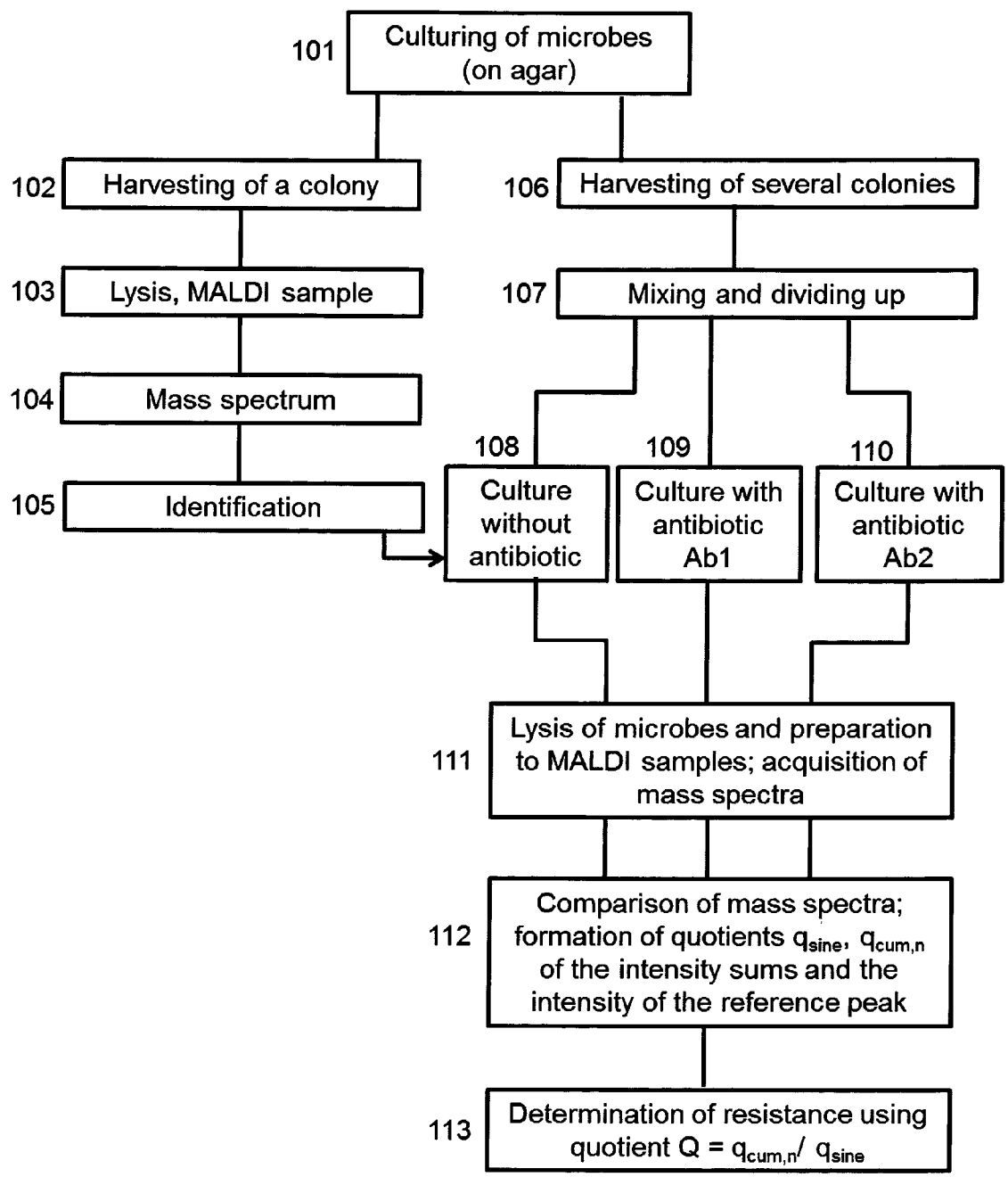
FIG. 1 shows an example of a flow diagram for a preferred method for identifying a microbe and determining its resistance according to this invention.
Figure 2:
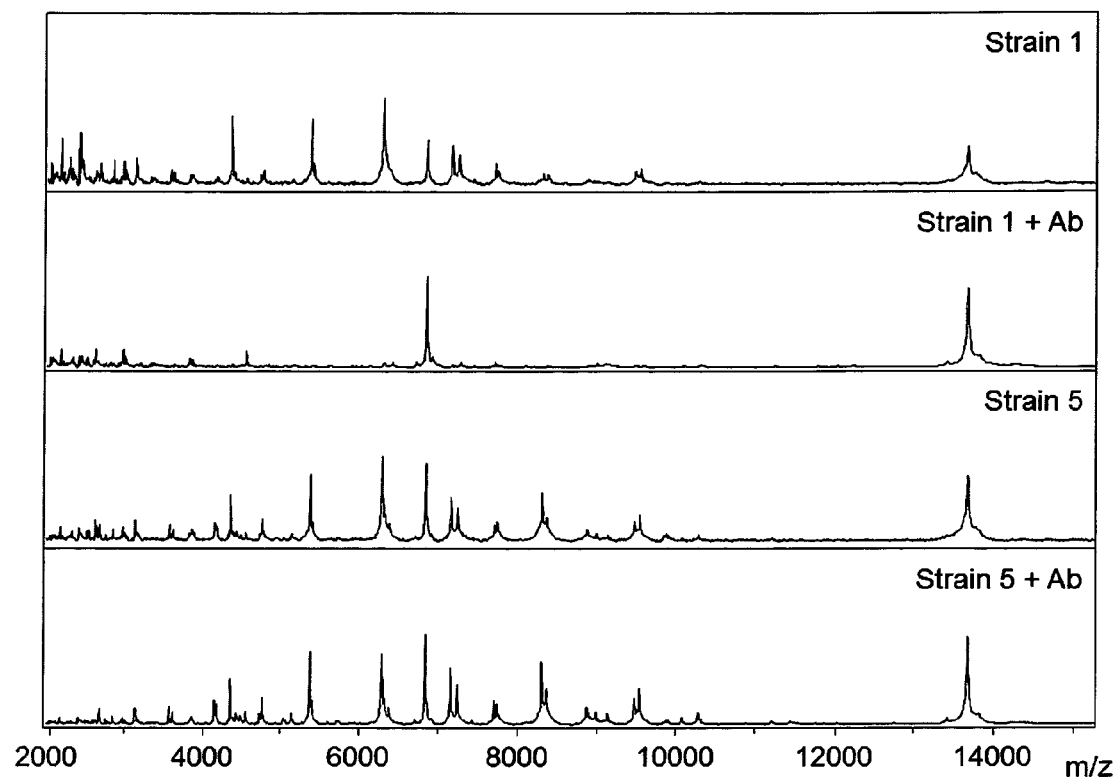
FIG. 2 shows four mass spectra of two strains of one species of bacteria of the genus *klebsiella*. The top two mass spectra originate from strain 1, which is susceptible, so no growth has occurred in the culture with the added antibiotic ("Ab"). In the second spectrum from the top ("strain 1+Ab"), practically only the mass peaks of the reference substance (ribonuclease A) are visible, singly charged on the far right, doubly charged slightly left of center. The bottom two mass spectra were obtained from strain 5, which is resistant, so the growth is uninhibited even when the antibiotic ("strain 5+Ab") is added (spectrum at the very bottom). All the mass spectra were acquired after a culture period of only one hour.
Figure 3:
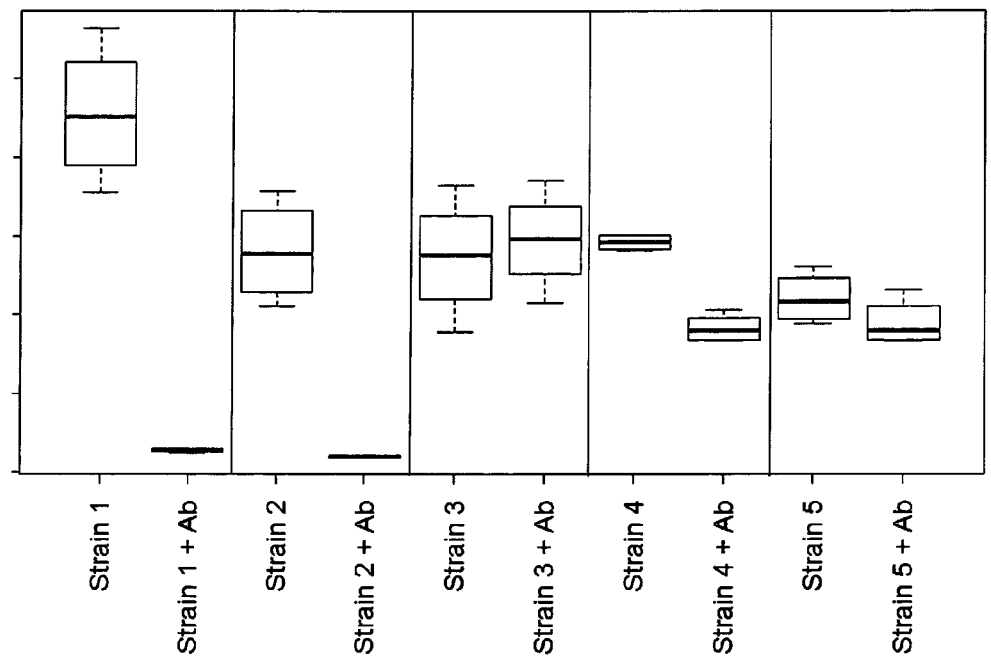
FIG. 3 illustrates an evaluation of the mass spectra of five *klebsiella* strains, in each case with and without antibiotic. Strain 1 and strain 2 are susceptible, therefore no growth in the presence of the antibiotic. Strains 3 and 5 are resistant, the same growth with and without antibiotic. For strain 4 it can be assumed either that an intermediate resistance is present or that only some of the harvested colonies are resistant, so the initial quantity of resistant microbes was smaller. The boxes represent the average variances for repeated measurements.

While the invention has been shown and described with reference to a number of embodiments thereof, it will be recognized by those skilled in the art that various changes in form and detail may be made herein without departing from the spirit and scope of the invention as defined by the appended claims.

The invention proposes a preferred method for the mass-spectrometric determination of the resistance of microbes by comparing the mass spectra of the microbes after culturing in several media of the same type, with and without the addition of antibiotics, wherein the microbial growth during culture is determined with the aid of at least one added reference substance, and microbial growth in a medium comprising antibiotic indicates resistance to this antibiotic at the given concentration. The microbes can in particular also be cultured in parallel in several (two or more) media with different types of antibiotic.

The reference substance can already be added at a dosed amount to the culture medium, which must then be of such a kind that it is always taken up by the microbes in the same quantity and is not decomposed, in order to be visible in the preparation after rinsing and cell lysis. Since this condition is difficult to fulfill, the reference substance is preferably added after culturing; for example it is added to the lysed cells or, in the case of ionization by matrix-assisted laser desorption, to the preparation of the sample on the sample support.

In order to determine the strength of the resistance or to determine whether or not the microbes of all colonies harvested are resistant in the same way, the microbes can be cultured in media comprising antibiotics at several concentration levels. If only some of the colonies harvested are resistant, for which the term "mixed resistance" is used here, then all levels of concentration exhibit the same proportionate reduction in growth compared to the culture without antibiotic, because the growth was started with a lower quantity of resistant microbes. This case is relatively rare, however. In the case of intermediate resistance, on the other hand, there is no longer any growth if the concentration of the antibiotic is high, but full growth if the concentration is low. It is also quite possible to not mix the microbes of the colonies, but to carry out these tests separately for the microbes of each colony Current practice is to cultivate microbes on agar or in a blood culture for identification, usually overnight. With agar cultures there are then usually several colonies, one of which is harvested for the identification. To determine the resistance, it is common practice to subject the microbes from at least five further colonies together to this test in order to also detect the presence of a resistant microbe colony among non-resistant microbe colonies of the same species (mixed resistance). A trained and experienced laboratory technician is generally able to recognize colonies of the same microbes and to harvest them. The microbes of these colonies can then preferably be mixed and divided up between the different cultures. But in special cases they can also be subjected to the resistance determination individually, for example if it cannot be assumed with certainty that the colonies belong to the same microbial species. Microbes from blood cultures naturally contain a mixture of different microbes which were transmitted in the infection. As those skilled in the art know, the blood culture usually ends in a centrifuge pellet which contains sufficient microbes for the identification and also for the resistance determination.

In one embodiment, the invention is similar to the method by Govorun, where mass spectra of the microbes from cultures with and without added antibiotics are compared with each other, but the invention is directed toward measurement of the microbial growth, which Govorun does not mention. In order to quantitatively determine the microbial growth in media with antibiotics with the aid of their mass spectra, one or more suitable, precisely dosed reference substances are added, preferably after the cell lysis. The increase in the biomass, and thus the associated increase in the proteins in particular, in the media with antibiotics is quantitatively determined with the aid of the reference substances. In particular, a comparison can be made here with the microbial growths in media without antibiotics, and also a comparison with the quantity of the microbes used without further culturing. An increase in the biomass to an expected extent shows that the microbes investigated are resistant to the antibiotics at the concentration used; susceptible microbes exhibit no growth if the concentration of the antibiotic is above the minimum inhibitory concentration (MIC).

Time-of-flight mass spectrometers with ionization by matrix-assisted laser desorption (MALDI) are mainly used for the identification. For decades, MALDI was deemed unsuitable for quantitative analyses. But it has long been shown that this is incorrect, and was attributable to the very coarse preparation methods used in the past for the samples on the sample support. It can be shown that the quantity of a substance can be determined with MALDI with an accuracy of two percent for a very good and uniform thin layer preparation and if reference substances are added in suitably precise doses, for example. Nothing like this degree of accuracy is required here; the effort which would have to be expended would also complicate the routine method unnecessarily. A quantitative accuracy of around 20 percent can also be achieved in a routine laboratory without much effort. Since the microbial growths in every doubling time involve a factor of two, i.e. for two doubling times a factor of four, MALDI is easily capable of fulfilling this task of measuring the microbial growths, even if the growth were to be slower in the presence of the antibiotic, or if not all the microbe colonies harvested are resistant.

The invention therefore proposes adding one or more substances which are suitable as quantitative references in suitable, accurately known quantities (or concentrations), for which the term "dosed" is used here, before measuring the mass spectra of the microbes. The reference substances can already be added to the culture medium; however, this then requires that the reference substance is preferably always taken up by the microbes in the same quantity and is not destroyed by digestion. It is therefore advantageous to add the dosed reference substances only after the microbes have been killed, either to the proteins in the liquid of the disrupted microbes in the centrifuge tube or to the matrix solution which is applied to the dried proteins on the MALDI sample support. These reference substances make it possible to quantitatively estimate the relative growth of the microbes with and without the addition of antibiotics, and to determine the resistance or susceptibility from this. The accuracy for the quantities and concentrations used should preferably be around 10 percent in order to maintain the overall accuracy of the method at around 20 percent. The reference substances should be easily ionizable due to a high proton affinity so that their ionization cannot be suppressed by the proteins of the microbes. Where possible, they should provide several easily recognizable peaks in the mass spectra. It is advantageous if the reference substances cover a larger range of quantities; three reference substances can be used in ratios of 100:10:1 or 25:5:1, for example. It has proved to be advantageous if the reference substance with the highest concentration produces reference signals in the mass spectrum which are around the same height (intensity) as exhibited by the highest microbe signals (usually protein signals) after full, uninhibited growth.

Ribonuclease A is cited here as an example of a substance which can be used successfully. It has a molecular weight of 13,638 daltons; its high proton affinity has the effect that singly, and also doubly and even triply, charged ions of ribonuclease A appear in the MALDI spectrum. The singly charged RNase-A ions appear in an area of the mass spectrum where they are easily recognizable, usually without interferences from other peaks.

Other ribonucleases can be given here as further suitable substances, for example. But it is also possible to use other substance classes with high proton affinity, for example lysozymes. Lysozyme C has a molecular mass of 14.3 kilodaltons, and so also has a peak in a sparsely populated range of the mass spectrum.

The method has proved to be surprisingly rapid: dangerous infections are usually caused by rapidly growing microbes with a doubling time of only about 20 minutes. Since only two generations of doubling are necessary to make the biomass grow by a factor of four, the resistance of these fast-growing microbes can already be identified after a culture period of only around 40 minutes; slower-growing microbes with 30 minutes doubling time require an hour. If one adds another 20 minutes for processing the microbes, preparation for MALDI ionization and acquiring the mass spectra, the resistance can be known in between one and one and a half hours after their identification. It is advantageous here that the microbes were identified before the determining the resistance. When the microbe species and its doubling time are known, the required culture period can be optimally specified.

The method further provides possibilities to check against mistakes made when the microbes are harvested or the samples prepared. The mass spectra of the microbes acquired after they have been cultured can be subjected once again to the identification routine for the microbes in order to confirm the correct assignment. Since this method of identification is time-consuming, it can be accelerated by simply determining the similarities between the mass spectra acquired after culturing and the mass spectrum which was used for the identification. The similarity values provide information on whether the correct mass spectra are present for determining the resistance.

Between full resistance of the microbes and full susceptibility there are intermediate stages; the growth is impaired, but not completely inhibited. In order to determine, or at least estimate, the strength of the resistance of microbes, the actual inhibitory concentrations of the antibiotics can be measured. The MIC values of the antibiotics (minimum inhibitory concentrations for fully susceptible microbes) are known to a large extent; the actual inhibitory concentrations increase with the strength of the resistance, however. To measure the actual inhibitory concentrations, cultures can be used to which an antibiotic at various concentration levels is added, wherein the concentration levels can correspond to the concentration 1*MIC, 10*MIC and 100*MIC of the known MIC values, for example. In our experience, the inhibition of microbial growth at a concentration of 1*MIC can only be detected with the method described above if the microbes are fully susceptible. In case of a weak resistance, the microbes are inhibited only at a concentration of 10*MIC, while for a very strong resistance, growth can still be detected even at a concentration of 100*MIC. The effect can be seen from the values of the microbial growths. With intermediate resistances there is therefore different growth at different concentrations of the antibiotic.

It can also be the case, however, that only a proportion, for example half, of the colonies harvested are resistant and the others are susceptible. We call this a "mixed resistance". Less growth then seems to be detected even with strong resistance, but only because there were a smaller number of resistant microbes in the culture at the start. If the test here is carried out with different concentrations of the antibiotic, all concentrations exhibit the same percentage reduction in protein growth compared to the culture without antibiotic If the method is carried out without concentration levels, a concentration of 10*MIC has proved to be particularly suitable.

To test the resistance to several antibiotics, it is possible to prepare several cultures with several antibiotics, where necessary even with different concentration levels of the antibiotics in each case. The additional time needed to prepare the microbes from several (two or more) cultures is of no consequence compared to the time required for the culture.

For a rapid test for multi-resistant germs (example: MRSA, methicillin-resistent *staphylococcus aureus*), a mixture of several types of antibiotics can be added to the media. If the microbes grow in this mixture, they are multiresistant. In this rapid test, a sample under investigation, such as a swab of the nasal mucosa, can also comprise a mixture of microbes and there is no need to identify the microbes in the sample beforehand. The mass spectrum acquired can be used to identify the microbes grown in the medium comprising antibiotic and thus determined as being resistant.

In a preferred embodiment, reactive substances are additionally added to the culture medium with the antibiotic in order to get a better accuracy of discrimination between resistant and susceptible microbes. The reactive substances can reactively modify microbes which are already weakened by the antibiotic and thus boost and assist the effect of the antibiotic. It is possible, for example, to add enzymes which can attack and destroy microbes whose growth has been affected while unaffected microbes cannot be attacked by the enzymes.

In a preferred method, the intensities of all the mass peaks in a selected section of the spectrum, for example from 4,000 to 10,000 daltons, are summed and divided by the intensity of the peak of the singly charged reference ions: this gives the quotient q. It is possible to refine the routine method for resistance determination in such a way that values of this quotient q under 200 represent susceptible peaks without growth (many of the peaks here are noise); while values of the quotient q above 200 indicate resistance. More preferable is an evaluation which forms the quotients $Q=q_{cum}/q_{sine}$ for microbes in media with antibiotics ($q_{cum}$) and without antibiotics ($q_{sine}$). If this quotient is close to one ($0.8<Q<1.3$), the microbes are resistant; Q is approximately 0.25 ($0.1<Q<0.4$) for susceptible germs if the culture period is around two doubling times.

In another preferred method, the mass spectrum $MS_{cum}$ acquired from microbes after they have been cultured in a medium with antibiotic is normalized to the maximum signal, if necessary after a base line subtraction. Multiple thresholds between zero and one are selected, preferably more than 10 and more preferably about 100 equidistant thresholds. For each threshold, peaks with intensity above the threshold are determined and the number of the determined peaks is assigned to the corresponding threshold resulting in a curve (numbers of peaks above threshold vs. threshold). The step of determining the number of peaks above threshold is preferably performed on a peak list obtained from the normalized and base line subtracted mass spectrum $MS_{cum}$. The area under the normalized curve (AUC) or the minimum distance between the point of origin and the curve can be determined as preferable measures for the microbial growth. An AUC above a specified value may indicate the resistance of the microbes against the antibiotic. More preferably, the AUC is also determined for $MS_{sine}$, i.e. the same signal processing is also applied to a mass spectrum $MS_{sine}$ of microbes which are cultivated under the same conditions, but without any antibiotic being present. A ratio $AUC(MS_{cum})/AUC(MS_{sine})$ above a specific value (preferably 4/10) indicates resistance against the antibiotic under investigation.

For routine laboratories with a larger number of microbe samples which must be both identified and tested for their resistance, it is valuable to be able to automate at least parts of the procedural steps. A complete automation of the whole method is currently not yet possible; there are, however, a number of instruments already on the market or under development and close to market readiness which can handle at least some procedural steps automatically or semi-automatically. There is an instrument which can harvest microbe colonies from agar plates either under visual control or by image analysis and which can apply the microbes onto the sample support plate for identification. This instrument can easily be developed further in order to also harvest microbes for determining the resistance. Instruments for lysing of microbes on the sample support plate and the preparation with matrix solution are also conceivable. Pipetting robots are available which can carry out the lysis of centrifuge pellets in suitable microtitration plates or in series of centrifuge tubes. Culturing can be carried out in centrifuge tubes (for example Eppendorf tubes) or in filter plates (for example Acropep 96-well filter plates). IVD-certified methods for MALDI mass spectrometers which operate with sample supports being able to hold 48, 96 or 384 samples are commercially available.

Ionization by matrix-assisted laser desorption (MALDI) requires either a sample support plate on which the matrix substance is already prepared in a thin layer, or preparation of a matrix solution. Commercially sold matrix substances often have the disadvantage that they are difficult to dissolve without ultrasound. Therefore, small bottles with purified and freeze-dried matrix substances in accurately dosed quantities are available, in which the matrix substance dissolves immediately when the solvent is added; the solution is ready to use immediately in the correct concentration. According to this invention, at least one reference substance for the quantification of protein increase can be added to the matrix substances of these products in the correct dose. In the device for the preparation of MALDI samples, the matrix solution can be applied to the dried cell components of the microbes, especially proteins, in a proper dose and without coming into contact with them. The sample support plates with thin matrix layers which are already sold commercially can also comprise reference substances in dosed amounts. The thin layers are each applied to small sample areas which are well separated from each other and each have a diameter of around two millimeters.

The sequence of a preferred method for determining resistances is shown in the diagram of FIG. 1 as an example. The method is shown here with the microbes being cultured on an agar (101). The microbes of a colony are harvested (102), disrupted (lysed), and processed into a MALDI sample (103). The acquisition of a mass spectrum (104) leads to the identification of the microbe by comparing its mass spectrum with reference spectra (105). In a routine laboratory it takes only 10 to 30 minutes from the harvesting of a colony through to the identification, depending on the number of microbe samples to be identified in parallel. It is possible to harvest several further colonies of the same microbe at the same time (106) in order to determine the resistance. These colonies are mixed and divided up between the different types of culture (107). Three cultures are prepared in the example shown in this diagram: one culture in a medium without antibiotic (108), and two cultures with the antibiotics Ab1 (109) and Ab2 (110). Of course, further cultures with further antibiotics and, if the strength of the resistance is also to be determined, cultures with different concentrations of the antibiotics can be prepared. All cultures are already prepared at the optimum temperature in order not to subject the microbes to a shock and so that the heating does not cause a time delay. The duration of the culture depends on the doubling time (generation time) of the microbes, which is known from the identification of the microbes. The culture only needs to last two to three doubling times. Around 40 minutes are sufficient for fast-growing microbes. The microbes from the different cultures are processed into MALDI samples with the addition of reference substances, and mass spectra are acquired (111). The quotient $q_{sine}$ is formed from the mass spectrum of the microbes which were cultured without antibiotics, by adding the intensities of all peaks in the mass range of 4,000 to 10,000 daltons, for example, and then dividing by the intensity of the reference peak. The corresponding quotients $q_{cum,n}$ are formed (112) from the mass spectra of the microbes which were cultured with the respective antibiotic n. As was stated above, the quotients $Q_n=q_{cum,n}/q_{sine}$ show the resistance in each case.

The methods have to date been carried out with ionization by MALDI in a MALDI time-of-flight mass spectrometer. MALDI has the great advantage that it forms almost only singly charged molecular ions. Therefore the mass spectra are not overloaded despite the 50 to 100 peaks which appear in the preferred mass range from 3,000 to 15,000 daltons, and similarities can be recognized relatively easily. This does not mean, however, that it is not possible to use other types of ionization. The spray-based methods, such as ESI (electrospray ionization) or DESI (direct surface ionization of solid samples by electrospray, desorption electrospray ionization), form multiply charged ions, which can easily overload the mass spectra, but they can be coupled with separation methods such as liquid chromatography (HPLC) or capillary electrophoresis (CE) so that it is possible to again obtain mass spectra with a simpler composition by separating the substances.

There are, however, other ionization methods which also produce almost only singly charged ions, for example chemical ionization (CI). Chemical ionization can be used in conjunction with neutral spray methods, but also with laser ablation of solid samples, and can be employed in conjunction with an OTOF-MS (time-of-flight mass spectrometer with orthogonal ion injection). The mass spectra thus obtained provide extremely high mass resolution with high sensitivity (cf. J. Franzen and K. Michelmann, DE 10 2005 044 307 B4, for example).

It is, of course, also possible to use other types of mass spectrometer if they provide the preferred mass range of 3,000 to 15,000 daltons for measuring the mass spectra.

Different aspects of the invention have been elucidated above. It will be understood, however, that various aspects or details of the invention may be changed, or that different aspects disclosed in conjunction with different embodiments of the invention may be readily combined if practicable, without departing from the scope of the invention. Furthermore, the foregoing description is for the purpose of illustration only, and not for the purpose of limiting the invention which is defined solely by the appended claims.

The invention claimed is:

1. A method for the mass-spectrometric determination of the resistance of microbes to an antibiotic, in which the microbes are cultured in a medium comprising the antibiotic, and a mass spectrum $MS_{cum}$ of the microbes is acquired after they have been cultured, the method comprising:
   providing at least one reference substance in a dosed amount that is measured together with the cultured microbes such that the mass spectrum $MS_{cum}$ comprises one or more reference mass signals of the at least one reference substance; and
   determining microbial growth taking place during the culture from the intensity of one or more microbe signals of the mass spectrum $MS_{cum}$, using the intensity of one or more of the reference mass signals as a quantitative reference, said microbial growth indicating the resistance to the antibiotic,
   wherein the mass spectrum $MS_{cum}$ is of the range of 2,000 to 15,000 daltons.

2. The method according to claim 1, wherein a quantity of microbes is standardized at the start of the culturing, and is subsequently determined after culturing from an intensity of one or more microbe signals of the mass spectrum $MS_{cum}$ using the intensity of one or more of the reference mass signals, and wherein the microbes are reported as being resistant to the antibiotic if the quantity of microbes exceeds a specified limit value.

3. The method according to claim 1, further comprising:
   preparing a second culture of the microbes in the medium without the antibiotic;
   acquiring a mass spectrum $MS_{sine}$ of the microbes of the second culture wherein the at least one reference substance is added in a dosed amount to the medium without antibiotic before, during or after culturing, or is added in a dosed amount during the preparation of the mass-spectrometric sample or during acquisition of the mass spectrum such that it is measured in the mass spectrum $MS_{sine}$; and
   determining the microbes as being resistant to the antibiotic if the quantities of microbes derived from the intensity of one or more microbe signals of the mass spectra $MS_{cum}$ and $MS_{sine}$ using the intensity of one or more reference signals of the mass spectra $MS_{cum}$ and $MS_{sine}$ as a quantitative reference differ in relative or absolute terms by less than a specified limit value.

4. The method according to claim 3, wherein the quantity of microbes is determined as a quotient from a mass spectrum, wherein the quotient is formed from one of
   the intensity of a microbe signal and the intensity of a reference signal,
   the intensity of a microbe signal and the summed intensities of several reference signals,
   the summed intensities of several microbe signals and the intensity of a reference signal,
   the summed intensities of several microbe signals and the summed intensities of several reference signals,
   the summed intensities of all the signals within one region or within the whole mass spectrum and the intensity of a reference signal, and
   the summed intensities of all the signals within one region or within the whole mass spectrum and the summed intensities of several reference signals.

5. The method according to claim 1, further comprising:
   acquiring an additional mass spectrum $MS_0$ of the microbes before the microbes are cultured;
   adding the at least one reference substance in a dosed amount to the medium or during the preparation of the mass-spectrometric sample or during acquisition of the mass spectrum such that it is measured in the mass spectrum $MS_0$; and
   determining the microbes as being resistant to the antibiotic if the quantity of microbes determined from the intensity of one or more microbe signals of the mass spectrum $MS_{cum}$ significantly exceeds the quantity of microbes being determined from the intensity of one or more microbe signals of the mass spectrum $MS_0$ using the intensity of one or more reference signals of the mass spectrum $MS_0$ as a quantitative reference.

6. The method according to claim 1, wherein the mass spectra are acquired by means of matrix-assisted laser desorption/ionization (MALDI), and the at least one reference substance is added during preparation of the MALDI samples on a sample support.

7. The method according to claim 1, wherein the microbes are cultured simultaneously in several cultures, each having a different antibiotic, and a mass spectrum $MS_{cum}$ is acquired for each culture.

8. The method according to claim 1, wherein the microbes are simultaneously cultured in several cultures, each having a different concentration of the antibiotic, and a mass spectrum $MS_{cum}$ is acquired for each culture.

9. The method according to claim 1, wherein the proton affinity of the at least one reference substance is greater than the proton affinity of most of the proteins of the microbes.

10. The method according to claim 9, wherein the at least one reference substance is a ribonuclease or a lysozyme.

11. The method according to claim 1, wherein the proteins of the microbes are concentrated before or during the preparation of a mass-spectrometric sample.

12. The method according to claim 1, wherein a mixture of reference substances is added in a dosed amount to the medium before, during or after culturing, or is added in a dosed amount during the preparation of the mass-spectrometric sample or during acquisition of the mass spectrum such that they are measured in the mass spectrum $MS_{cum}$.

13. The method according to claim 12, wherein the reference substances of the mixture are present in different concentrations which differ by a factor between 5 and 100.

14. The method according to claim 1, wherein the microbes are identified taxonomically before their resistance is determined, and the at least one reference substance, limit values for determining the resistance, the medium and the culture conditions are selected on the basis of the taxonomic classification.

15. The method according to claim 1, wherein the mass spectra are acquired by means of matrix-assisted laser desorption/ionization (MALDI).

16. The method according to claim 15, wherein multiple MALDI samples are prepared on a sample support on which a matrix substance is already prepared in a layer wherein the layer has a dosed addition of a reference with a mass of between 10 and 20 kilodaltons.

17. The method according to claim 1, wherein the mass of the at least one reference substance is between 10 and 20 kilodaltons.

18. A method for the mass-spectrometric determination of the resistance of microbes to an antibiotic, in which the microbes are cultured in a medium comprising the antibiotic, and a mass spectrum of the microbes is acquired after they have been cultured, wherein:

at least one reference substance is added in a dosed amount to the medium before, during or after culturing, or is added in a dosed amount during the preparation of the mass-spectrometric sample or during acquisition of the mass spectrum such that it is measured as at least one reference mass signal in the mass spectrum;

microbial growth is ascertained by determining the quantity of microbes after culturing from the mass spectrum and then comparing this quantity with a correspondingly determined or standardized quantity of microbes before culturing and/or with a correspondingly determined quantity of microbes after culturing without the antibiotic; and microbial growth indicates the resistance to the antibiotic, wherein the quantity of microbes is determined from the intensity of the at least one reference mass signal of the at least one reference substance, and the mass spectrum is of the range of 2,000 to 15,000 daltons.

19. The method according to claim 18, wherein the mass spectra are acquired by means of matrix-assisted laser desorption/ionization (MALDI).

20. The method according to claim 19, wherein the mass of the at least one reference substance is between 10 and 20 kilodaltons.

* * * * *